US00PP24518P2

(12) United States Plant Patent
Koppe

(10) Patent No.: US PP24,518 P2
(45) Date of Patent: Jun. 3, 2014

(54) *BEGONIA* PLANT NAMED 'DARDORAN IMP'

(50) Latin Name: *Begonia×hiemalis*
Varietal Denomination: Dardoran Imp

(75) Inventor: Lubbertus H. Koppe, Putten (NL)

(73) Assignee: Koppe Royalty B.V., Putten (NL)

( * ) Notice: Subject to any disclaimer, the term of this patent is extended or adjusted under 35 U.S.C. 154(b) by 47 days.

(21) Appl. No.: 13/573,169

(22) Filed: Aug. 27, 2012

(51) Int. Cl.
*A01H 5/00* (2006.01)

(52) U.S. Cl.
USPC ..... Plt./347

(58) Field of Classification Search
USPC ..... Plt./347
See application file for complete search history.

*Primary Examiner* — Annette Para
(74) *Attorney, Agent, or Firm* — C. A. Whealy

(57) ABSTRACT

A new and distinct cultivar of *Begonia* plant named 'Dardoran Imp' characterized by its compact, upright, outwardly spreading and mounded plant habit; freely branching habit; dark green-colored leaves; numerous orange-colored double flowers that are held above and beyond the foliar plane; and excellent postproduction longevity.

2 Drawing Sheets

Botanical designation: *Begonia×hiemalis.*
Cultivar denomination: 'DARDORAN IMP'.

BACKGROUND OF THE INVENTION

The present invention relates to a new and distinct cultivar of *Begonia* plant, botanically known as *Begonia×hiemalis*, commercially known as Elatior *Begonia* and hereinafter referred to by the name 'Dardoran Imp'.

The new *Begonia* plant is a naturally-occurring whole plant mutation of *Begonia×hiemalis* 'Dardoran', not patented. The new *Begonia* plant was discovered and selected by the Inventor as a single flowering plant from within a population of plants of 'Dardoran' in a controlled greenhouse environment in Ermelo, The Netherlands in July, 2008.

Asexual reproduction of the new *Begonia* plant by vegetative cuttings taken in a controlled greenhouse environment in Ermelo, The Netherlands since November, 2008 has shown that the unique features of this new *Begonia* plant are stable and reproduced true to type in successive generations.

SUMMARY OF THE INVENTION

Plants of the new *Begonia* have not been observed under all possible environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Dardoran Imp'. These characteristics in combination distinguish 'Dardoran Imp' as a new and distinct *Begonia* plant:

1. Compact, upright, outwardly spreading and mounded plant habit.
2. Freely branching habit.
3. Dark green-colored leaves.
4. Numerous orange-colored double flowers that are held above and beyond the foliar plane.
5. Excellent postproduction longevity.

Plants of the new *Begonia* differ primarily from plants of the parent, 'Dardoran', in flower color. Plants of the new *Begonia* have darker orange-colored flowers than plants of 'Dardoran'.

Plants of the new *Begonia* can be compared to plants of *Begonia×hiemalis* 'Reina', disclosed in U.S. Plant Pat. No. 19,336. In side-by-side comparisons conducted in Ermelo, The Netherlands, plants of the new *Begonia* differed primarily from plants of 'Reina' in flower color and form as plants of 'Reina' had slightly darker orange-colored flowers with fewer tepaloids.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical flowering plant of 'Dardoran Imp' grown in a container.

The photograph on the second sheet are close up views of the upper and lower surfaces of typical leaves (right) and upper, lateral and lower surfaces of developing and open flowers of 'Dardoran Imp' (left).

DETAILED BOTANICAL DESCRIPTION

The aforementioned photographs and following observations and measurements describe plants grown during the spring in 13-cm containers in a glass-covered greenhouse in Ermelo, The Netherlands and under cultural practices typical of commercial *Begonia* production. During the production of the plants, day temperatures averaged 20° C. and night temperatures averaged 18° C. Plants were pinched one time and were twelve weeks old when the photographs and description were taken. In the following description, color references are made to The Royal Horticultural Society Colour Chart, 2007 Edition, except where general terms of ordinary dictionary significance are used.

Botanical classification: *Begonia×hiemalis* 'Dardoran Imp'.

Commercial classification: Elatior *Begonia*.

Parentage: Naturally-occurring whole plant mutation of *Begonia×hiemalis* 'Dardoran', not patented.

Propagation:

*Type*.—By terminal vegetative cuttings.

*Time to develop roots*.—About 20 days at temperatures of 20° C.

*Time to produce a rooted young plant*.—About five weeks at temperatures of 20° C.

*Root description*.—Fine, fibrous; white to orange brown in color.

*Rooting habit*.—Freely branching; medium density; plants of the new *Begonia* have not been observed to form tubers.

Plant description:

*Plant habit and form*.—Compact, upright, outwardly spreading and mounded plant habit; overall plant shape roughly globular; flowers held above and beyond the foliar plane.

*Growth habit*.—Moderately vigorous growth habit and moderate growth rate; suitable for 12-cm and larger containers; under optimal environmental and cultural conditions, usually about twelve weeks are required to produce proportional 13-cm potted plants from cuttings; vegetative shoots are formed at basal nodes and flowering shoots are formed at upper nodes.

*Branching habit*.—Freely branching habit; when pinched, about six lateral branches develop.

*Plant height*.—About 24.5 cm.

*Plant width*.—About 36.9 cm.

*Lateral branches*.—Length: About 14.1 cm. Diameter: About 8 mm. Internode length: About 1.9 cm. Angle: About 45° from vertical. Texture: Smooth, sparsely pubescent. Color, developing: Close to 146C to 146D. Color, fully developed: Close to 148A.

*Leaves*.—Arrangement: Alternate; simple. Length: About 11.6 cm. Width: About 9.9 cm. Shape: Broadly ovate. Apex: Broadly acute. Base: Oblique. Margin: Bi-serrate; laciniate. Texture, upper and lower surfaces: Smooth, glabrous; velvety. Venation pattern: Palmate. Color: Developing leaves, upper surface: Darker than between 147A and N199A. Developing leaves, lower surface: Close to 187B. Fully expanded leaves, upper surface: Darker than between 147A and N189A; venation, close to 144A. Fully expanded leaves, lower surface: Close to 183A to 183B; venation, close to 146A to 146B. Petioles: Length: About 5.4 cm. Diameter: About 4.5 mm. Texture, upper and lower surfaces: Sparsely pubescent. Color, upper surface: Close to 174A; at leaf attachment, close to 178A to 178B. Color, lower surface: Close to 177B. Stipules: Length: About 1 cm. Width: About 1.1 cm. Shape: Broadly ovate. Margin: Entire. Texture, upper and lower surfaces: Smooth, glabrous. Color, upper and lower surfaces: Close to 144B; venation, close to 144A.

Flower description:

*Flower form and flowering habit*.—Double rotate flowers arranged in axillary compound cymes; usually about 16 flowers per cyme, numerous cymes in flower simultaneously and about 480 flowers developing per plant; flowers face upright to outwardly and are positioned above and beyond the foliar plane.

*Natural flowering season*.—Plants begin flowering about six weeks after pinching; plants flower continuously year round regardless of nyctoperiod, however plants are more freely flowering from autumn to spring.

*Flower longevity*.—Individual flowers last about ten days on the plant; flowers not persistent; flowering plants have excellent postproduction longevity and typical maintain good substance for about seven weeks under interior conditions.

*Fragrance*.—None detected.

*Inflorescence height*.—About 16 cm.

*Inflorescence diameter*.—About 14.1 cm.

*Flower buds*.—Length: About 1.9 cm. Diameter: Ranging from about 5 mm to 20 mm. Shape: Reniform, flattened. Color: Close to 47C.

*Flowers*.—Shape: Rotate; double. Diameter: About 6.6 cm. Depth (height): About 3.3 cm.

*Tepals*.—Quantity per flower: About four arranged in a single whorl. Length: About 3.5 cm. Width: About 4.2 cm. Shape: Roughly orbicular. Apex: Rounded. Margin: Entire. Texture, upper and lower surfaces: Smooth, glabrous; slightly velvety. Color: When opening, upper surface: Close to 30C to 30D. When opening, lower surface: Close to 35A to 35B; towards the base, close to 29C. Fully opened, upper surface: Close to 35B; towards the base, close to 29A; with development, color becoming closer to 35C and towards the base, close to 26C. Fully opened, lower surface: Close to 39B to 39C; with development, color becoming closer to 39C.

*Tepaloids*.—Quantity per flower: About 14 arranged in several whorls. Length: About 2.5 cm. Width: About 1.9 cm. Shape: Obovate to broadly elliptic. Apex: Rounded. Margin: Entire. Texture, upper and lower surfaces: Smooth, glabrous; slightly velvety. Color: When opening, upper surface: Close to 30C to 30D. When opening, lower surface: Close to 35A to 35B; towards the base, close to 29C. Fully opened, upper surface: Close to 35B; towards the base, close to 29A; with development, color becoming closer to 35C and towards the base, close to 26C. Fully opened, lower surface: Close to 39B to 39C; with development, color becoming closer to 39C.

*Peduncles*.—Length: About 6.1 cm. Diameter: About 5 mm. Angle: About 45° from lateral branch axis. Texture: Smooth, glabrous. Color: Between 144A and 144B.

*Pedicels*.—Length: About 3.1 cm. Diameter: About 2.5 mm. Angle: About 40° from peduncle axis. Texture: Smooth, glabrous. Color: Close to 152D; towards the base, close to 144B.

*Reproductive organs*.—Stamens: None observed. Pistils: None observed.

*Seeds and fruits*.—Seed and fruit development have not been observed on plants of the new *Begonia*.

Disease & pest resistance: Resistance to pathogens and pests common to *Begonia* has not been observed on plants of the new *Begonia*.

Temperature tolerance: Plants of the new *Begonia* have been observed to tolerate high temperatures of about 35° C. and to be hardy to USDA Hardiness Zone 10.

It is claimed:

1. A new and distinct *Begonia* plant named 'Dardoran Imp' as illustrated and described.

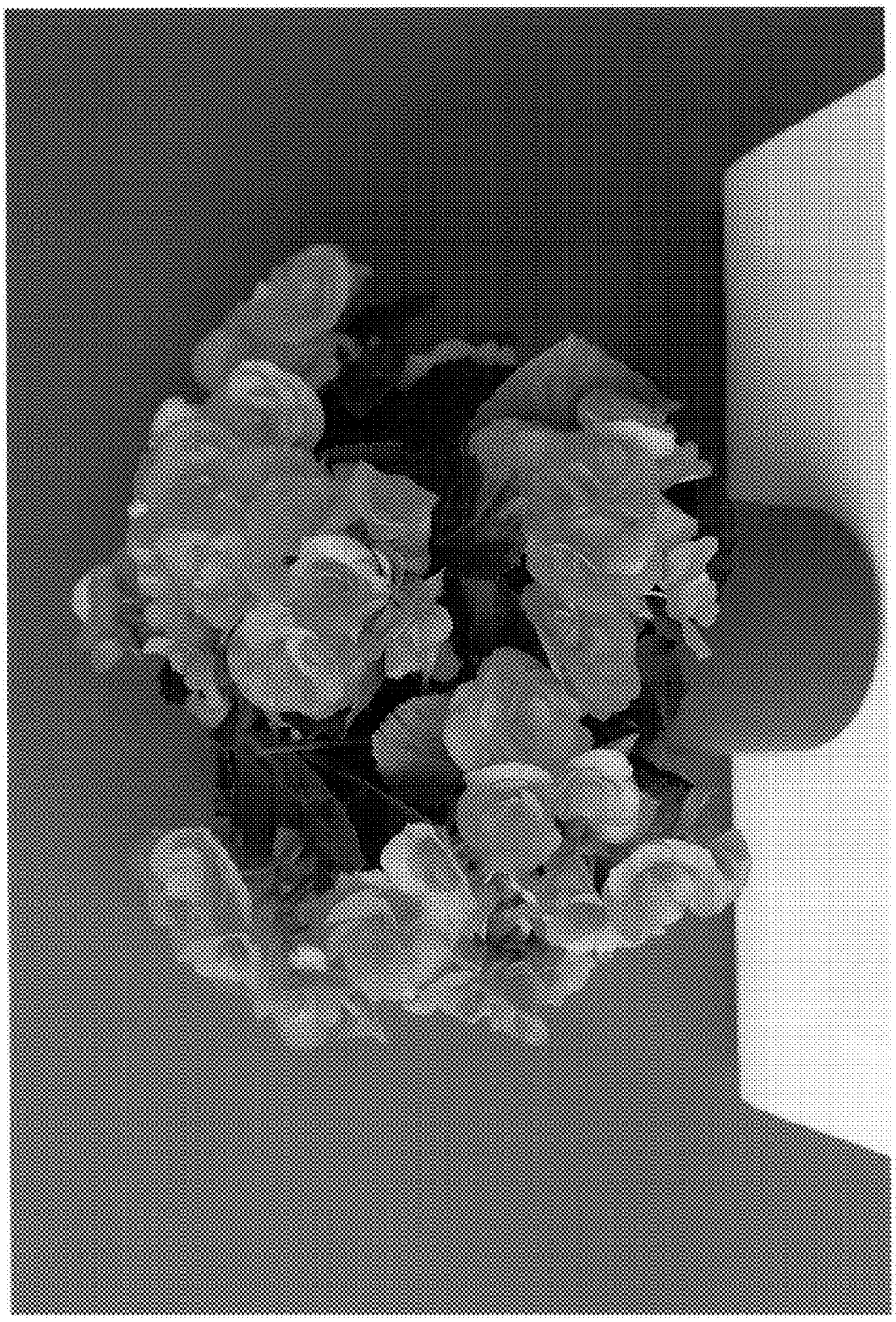

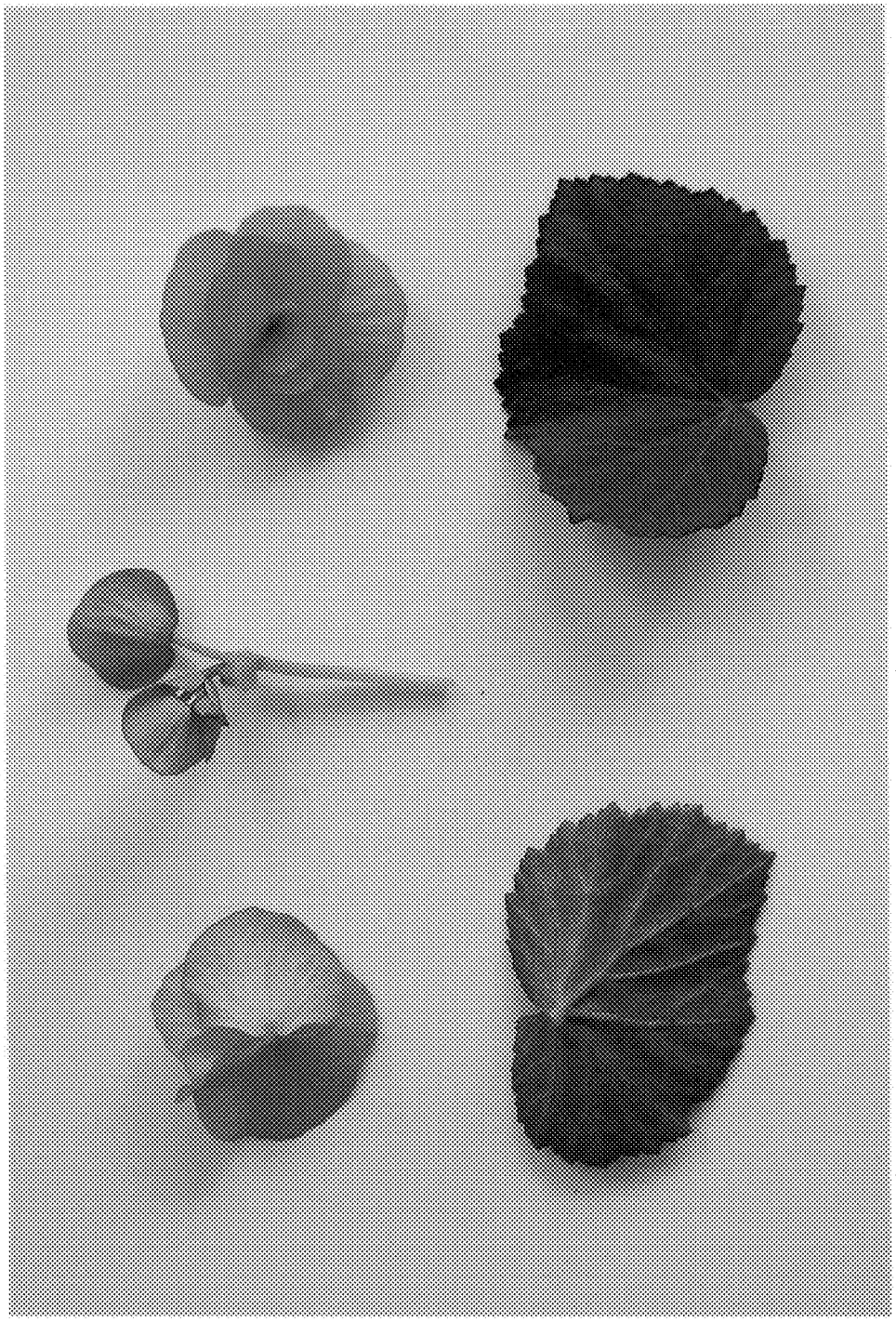

* * * * *